United States Patent [19]
Broeker et al.

[11] Patent Number: 5,414,113
[45] Date of Patent: May 9, 1995

[54] PROCESS FOR RECOVERY OF AROMATIC ACID FROM WASTE POLYESTER RESIN

[75] Inventors: Jeffrey L. Broeker; John A. Macek, both of Naperville; Mossman: Allen B., Wheaton; Bruce I. Rosen, Morton Grove; Thomas M. Bartos, Naperville, all of Ill.

[73] Assignee: Amoco Corporation, Chicago, Ill.

[21] Appl. No.: 138,917

[22] Filed: Oct. 18, 1993

[51] Int. Cl.⁶ .............................................. C07C 51/16
[52] U.S. Cl. ................................... 562/413; 562/416; 562/483; 562/487
[58] Field of Search ................. 562/483, 487, 413, 416

[56] References Cited

U.S. PATENT DOCUMENTS

| | | | |
|---|---|---|---|
| 3,488,298 | 1/1970 | Barkey et al. | 260/2.3 |
| 3,728,287 | 4/1973 | Bermaster | 260/2.3 |
| 4,124,666 | 11/1978 | Wilhelm et al. | 264/39 |
| 4,163,860 | 8/1979 | Delattre et al. | 560/96 |
| 4,355,175 | 10/1982 | Pusziaszeri | 562/483 |
| 4,578,510 | 3/1986 | Doerr | 562/483 |
| 4,605,762 | 8/1986 | Mandoki | 562/483 |
| 4,620,032 | 10/1986 | Doerr | 562/483 |
| 5,045,122 | 9/1991 | Tindall et al. | 134/29 |
| 5,051,528 | 9/1991 | Naujokas | 562/483 |
| 5,095,145 | 3/1992 | Rosen | 562/483 |
| 5,200,557 | 4/1993 | Gee et al. | 562/486 |
| 5,328,982 | 7/1994 | Tindall | 562/483 |

FOREIGN PATENT DOCUMENTS 2123403  2/1984  United Kingdom .

Primary Examiner—Michael L. Shippen
Attorney, Agent, or Firm—Thomas E. Nemo; Wallace L. Oliver

[57] ABSTRACT

Processes are disclosed for recovery and purification of dibasic aromatic acids from waste polyester film, fiber, bottles, manufacturing residues, and other manufactured articles. The processes comprises: depolymerizing polyester resin in a solvent under conditions suitable for hydrolysis of ester bonds to obtain a mixture containing a solution of aromatic acid and impurities consisting of alcohol and/or other components of the resin; burning impurities in a liquid-phase oxidation with an oxygen-containing gas in the presence of an oxidation catalyst at elevated pressures and temperatures, to obtain an oxidation product containing the desired aromatic acid; and crystallizing and separating from the oxidation system a resulting crude dibasic aromatic acid. Crude acid is, optionally, hydrogenated in an aqueous solution at elevated temperatures and pressures in the presence of hydrogen and an insoluble metal-containing catalyst, which is thereupon separated from the aqueous solution, and purified dibasic aromatic acid recovered by crystallization and mechanical separation from the aqueous solution. Purified terephthalic acid has, typically, a $L^*$-value in a range of from about 95 to about 100, an $a^*$-value in a range of from about $-1$ to about $+1$, and a $b^*$-value in a range of from about 0.5 to about 2.

21 Claims, No Drawings

PROCESS FOR RECOVERY OF AROMATIC ACID FROM WASTE POLYESTER RESIN

FIELD OF THE INVENTION

The field of this invention relates to preparation of aromatic acids from waste polyester resin by processes including production and/or recovery of aromatic carboxylic acid from polyester resin comprising repeating units of aromatic acid residue and repeating units of dihydric alcohol residue linked by ester bonds which processes include hydrolysis of the ester bonds and liquid-phase oxidation. More particularly, this invention concerns a recovery process comprising: depolymerizing polyester resin in a solvent to obtain a mixture containing a solution of aromatic acid and impurities consisting of alcohol and other components of the resin; burning at least a portion of the impurities in a liquid-phase oxidation with an oxygen-containing gas in the presence of an oxidation catalyst, to obtain an oxidation product containing the aromatic acid; and crystallizing and separating a crude dibasic aromatic acid from the liquid phase. Crude acid is, advantageously, hydrogenated in an aqueous solution in the presence of hydrogen and an insoluble metal-containing catalyst which is thereupon separated from the aqueous solution. Thereafter purified dibasic aromatic acid is crystallized and separated from the aqueous solution.

In one aspect this invention relates to processes for manufacture of terephthalic acid which processes including both recovering terephthalic acid from waste polyethylene terephthalate resin and forming terephthalic acid by liquid-phase oxidation of para-xylene. Processes, for example, in which crude terephthalic acid is obtained by simultaneous reaction of polyethylene terephthalate and para-xylene together in one or more zones under conditions of liquid-phase oxidation. Hydrogenation of crude terephthalic acid in an aqueous solution reduces organic impurities contained in terephthalic acid which is recovered by crystallization and separation from the aqueous solution.

In another aspect this invention relates to processes for manufacture 2,6-naphthalene dicarboxylic acid which processes include both recovering 2,6-naphthalene dicarboxylic acid from waste from poly(ethylene-2,6-naphthalene) resin and forming 2,6-naphthalene dicarboxylic acid by liquid-phase oxidation of 2,6-dimethyl naphthalene. Processes, for example, in which include depolymerization of poly(ethylene-2,6-naphthalene) resin and liquid-phase oxidation 2,6-dimethyl naphthalene.

BACKGROUND OF THE INVENTION

Aromatic dicarboxylic acids are well known starting materials for making polyester resins, which polyester resins are used widely as principal polymers for polyester fibers, polyester films, and resins for bottles and like containers. For a polyester resin to have properties required in many of these uses, the polyester resin must be made from a polymer grade or "purified" aromatic acid, such as purified terephthalic acid.

Purified terephthalic acid is derived from relatively less pure, technical grade or "crude" terephthalic acid by purification of the latter utilizing hydrogen and a noble metal catalysts as described in U.S. Pat. No. 3,584,039 to Meyer. In the purification process, impure terephthalic acid is dissolved in water at an elevated temperature, and the resulting solution is hydrogenated, preferably in the presence of a hydrogenation catalyst, e.g., palladium on a carbon support, as described in U.S. Pat. No. 3,726,915 to Pohlmann. This hydrogenation step converts various color bodies present in the relatively impure terephthalic acid to colorless products. Another related purification-by-hydrogenation process of aromatic polycarboxylic acids produced by liquid phase catalyst oxidation of polyalkyl aromatic hydrocarbons is described in U.S. Pat. No. 4,405,809 to Stech et al.

Depolymerization of polyethylene terephthalate by hydrolysis at a high temperature and pressure in the absence of a base or acid, or a catalyst, is known, see for example, U.S. Pat. No 4,521,556; U.S. Pat. No 4,587,502; U.S. Pat. No 4,605,762; GB. Patent No 2,123,403; U.S. Pat. No 4,578,510; U.S. Pat. No 4,620,032; U.S. Pat. No 4,626,598; Japanese Patent No. 49020147; and Japanese Patent No. 56118420. Depolymerization of polyethylene terephthalate By hydrolysis under conditions of neutral pH can, however, result in production of oligomeric co-products (U.S. Pat. No. 4,578,510); derivatives of terephthalic acid (Wolkrna Chem., 13(2), 144–55); and/or cyclic trimers (Japanese Patent No. 56118420). Additionally, depolymerization product of waste polyethylene terephthalate in the form of Bottles, film, fiber and other manufactured articles usually contain dyes and contaminants (U.S. Pat. No 4,521,556; GB. Patent No 2,123,403; and Japanese Patent No. 49020147). Accordingly, although various processes are available for hydrolyzing polyethylene terephthalate waste, the purification of recovered terephthalic acid typically requires several process steps to remove dyes, pigments, and other impurities including inorganic compounds such as catalyst residues and organic compounds winch can result from depolymizeration reactions.

U.S. Pat. No 4,335,175, to Pusztaszeri, exemplifies some difficulties encountered in preparing a purified terephthalic acid from polyethylene terephthalate waste. Polyester scrap such as film (with or without silver), fabric, yarn, or bottles, was depolymerized at ambient temperatures with a mixture of concentrated sulfuric acid and water to form crude terephthalic acid. Pusztaszeri states that an alkaline solution, which can be dark brown or black in color, containing crude terephthalic acid resulting from the depolymerization, is filtered to obtain a clear liquid which many be light brown in color(if colored, it must be treated with activated charcoal and filtered from the charcoal). The resulting solution is then acidified with sulfuric acid to precipitate the terephthalic acid. Terephthalic acid is then recovered by filtration and washed.

Recently, in U.S. Pat. No 5,095,145, to Rosen, a process is disclosed for preparing a purified terephthalic acid from waste polyethylene terephthalate. Scrap was depolymerized at temperatures of from about 221° C. to about 316° C. with water at pressures sufficient to maintain a liquid phase and, subsequent to cooling, a crude terephthalic acid filter cake was recovered from the resulting solution and washed. The cake was reslurried and dissolved in water. Thereupon, the solution obtained was catalytically hydrogenated at temperatures of from about 221° C. to about 316° C. at pressures sufficient to maintain a liquid phase for a period of up to 8 hours. Rosen states that pellets of green waste polyethylene terephthalate from waste green bottles were depolymerized by this process at 274° C. and samples of crude terephthalic acid filter cakes taken after 2 hours and a longer period. After filter cakes of terephthalic acid from green bottles were analyzed for color, $L^*$-values of 91.54 and 68.18, $a^*$-values of $-0.55$ and 1.22, and $b^*$-values of 5.22 and 15.88, respectively, were reported. In Example XII of U.S. Pat. No 5,095,145 it is stated that hydrogenation of crude terephthalic acid from waste green polyethylene terephthalate required up to about 6 hours to reduce initial $b^*$-values greater than 2 but less than 10 to less than 2. The reported $L^*$-value, however, increased to over 95 and $a^*$-values also increased, but remained negative.

Regardless of the methods of depolymerization and purification of resulting terephthalic acid, the variable nature of crude terephthalic acid obtained from depolymerization of polyethylene terephthalate waste from many sources and the variable nature of impurities resulting therefrom and contained in the crude terephthalic acid, the process control and thus quality assurance of the purified terephthalic acid, has been made difficult and costly. Because of this lack of quality assurance and its cost relative to that of virgin purified terephthalic acid, purified terephthalic acid from polyethylene terephthalate waste has not been considered as a viable economic replacement for fiber grade virgin purified terephthalic acid prepared from para-xylene.

It is therefore a general object of the present invention to provide an improved method which overcomes the aforesaid problem of prior art methods, for recovery of aromatic acid from polyester resin which has been used for polyester fibers, polyester films, and resins in bottles and like containers.

More particularly, it is an object of the present invention to provide an improved method for recovery from polyester resins aromatic acid sufficiently free of undesired impurities so that the acid can be used to make polyester resins which have good color and other properties needed in manufacture of commercial articles.

Other objects and advantages of the invention will become apparent upon reading the following detailed description and appended claims.

SUMMARY OF THE INVENTION

Economical processes are disclosed for recovering dibasic aromatic acid from polyester resin comprising repeating units of dibasic aromatic acid residue and repeating units of dihydric alcohol residue linked by ester bonds. In one embodiment of this invention, a dibasic aromatic acid is produced by a process which comprises: (A) depolymerizing polyester resin in a solvent under conditions suitable for hydrolysis and/or alcohololysis of ester bonds to form a mixture containing a solution of aromatic acid and impurities consisting of alcohol and other components of the resin; (B) burning at least a portion of the impurities in a liquid-phase oxidation with an oxygen-containing gas in the presence of an oxidation catalyst at elevated pressures and temperatures in an oxidation solvent system consisting of a $C_2$ to $C_6$ monocarboxylic acid, water, or a mixture thereof, to form an oxidation product containing aromatic acid; and (C) separating from the oxidation solvent system resulting solid product of crude dibasic aromatic acid substantially free of alcohol, but containing organic impurities. Both the depolymerizing of polyester resin and the liquid phase oxidation can be carried out together in one or more reaction zones.

Where aromatic acid product of higher purity is desired, processes for recovering dibasic aromatic acid from polyester resin according to this invention, further comprises: (D) reducing at least a portion of the organic impurities in the crude dibasic aromatic acid in an aqueous solution at elevated temperatures and pressures and in the presence of hydrogen and at least one insoluble Group VIII noble metal-containing catalyst; (E) separating the solid noble metal-containing catalyst from the aqueous solution; and (F) crystallizing and separating purified dibasic aromatic acid from the aqueous solution while maintaining the temperature in a range of from about 25° C. to about 150° C.

Fiber-grade terephthalic acid is, generally, obtained using a hydrogenation catalyst in which the noble metal is at least one member of the group consisting of palladium and rhodium. Purified terephthalic acid produced from waste polyethylene terephthalate according to this invention has a total metals content of less than 100 ppm and contains less than 1000 ppm total of 4-carboxybenzaldehyde and para-toluic acid.

In another embodiment of this invention, terephthalic acid is produced by a process which comprises: (A) depolymerizing polyethylene terephthalate resin comprising repeating units of terephthalic acid residue and repeating units of ethylene glycol residue linked by ester bonds, in a solvent comprising of a $C_1$ to $C_6$ alcohol, water, or a mixture thereof, under conditions suitable for hydrolysis of ester bonds at temperatures in a range of from about 120° C. to about 320° C. and pressures sufficient to maintain a liquid phase, to form a depolymerization solution consisting of terephthalic acid, ethylene glycol, and impurities comprising components derived from the resin; (B) burning at least a portion of the impurities in a liquid-phase oxidation with an oxygen-containing gas in the presence of an oxidation catalyst comprising a cobalt containing component at elevated pressures and temperatures in an oxidation solvent system comprising a $C_2$ to $C_6$ monocarboxylic acid, water, or a mixture thereof, to form an oxidation product containing terephthalic acid; and (C) crystallizing and separating from the oxidation solvent system resulting crude terephthalic acid having a total metals content of less than 100 ppm, but containing organic impurities comprising aromatic aldehydes and/or monocarboxylic aromatic acids having one or more substituent methyl group, while maintaining a temperature in a range of from about 50 ° C. to about 150 ° C.

Processes for recovering terephthalic acid from polyethylene terephthalate resin, advantageously, further comprise: crystallizing and separating from the depolymerization solution a recovered terephthalic acid substantially free of ethylene glycol, but containing color-causing impurities, prior to burning at least a portion of the color-causing impurities in a liquid-phase oxidation.

In preferred embodiment of this invention, terephthalic acid is produced by a process which further comprises: forming terephthalic acid in a liquid phase oxidation of para-xylene. Both the burning of impurities and the oxidation of para-xylene are, advantageously, carried out at temperatures in a range of from about 120° C. to about 240° C. in the presence of an oxidation catalyst comprising cobalt, manganese, and bromine components in a solvent system comprising acetic acid containing from 1 weight percent to 20 weight percent of water in the liquid phase.

Both the burning of impurities and the forming terephthalic acid by liquid phase oxidation of para-xylene are, preferably, carried out together in one or more reaction zones.

Likewise, the depolymerizing of polyethylene terephthalate resin, the burning of impurities and the forming terephthalic acid by liquid phase oxidation of para-xylene can be carried out together in one or more reaction zones.

Processes for recovering terephthalic acid from polyethylene terephthalate resin, with or without liquid phase oxidation of paraxylene, advantageously, further comprises: (D) reducing at least a portion of the organic impurities in the crude terephthalic acid in an aqueous solution at elevated temperatures and pressures and in the presence of hydrogen and at least one insoluble Group VIII noble metal-containing catalyst; (E) separating the solid noble metal-containing catalyst from the aqueous solution; and (F) crystallizing and separating purified terephthalic acid from the aqueous solution while maintaining the temperature in a range of from about 50 ° C. to about 150 ° C.

When the insoluble metal-containing catalyst has a palladium containing component on a carbon support, terephthalic acid produced from waste polyethylene terephthalate according to this invention has a total metals content of less than 10 ppm, and color measured by a L*-value greater than about 95, preferably in a range of from about 95 to about 100, an a*-value greater than about $-1.5$, preferably in a range of from about $-1$ to about $+1$, and a b*-value less than about 2, preferably in a range of from about 0.5 to about 2.

In yet another embodiment of this invention, terephthalic acid is produced by a process which comprises: (1) depolymerizing waste polyethylene terephthalate resin comprising repeating units of terephthalic acid residue and repeating units of ethylene glycol residue linked by ester bonds, in a solvent comprising of a $C_1$ to $C_6$ alcohol, water, or a mixture thereof, under conditions suitable for hydrolysis of ester bonds at temperatures in a range of from about 120° C. to about 320° C. and pressures sufficient to maintain a liquid phase, to form a depolymerization solution consisting of terephthalic acid, ethylene glycol, and impurities comprising copper containing components derived from the resin; (2) crystallizing and separating from the depolymerization solution a recovered terephthalic acid substantially free of ethylene glycol, but containing impurities comprising copper containing components derived from the resin; (3) burning at least a portion of the impurities in a liquid-phase oxidation with an oxygen-containing gas in the presence of an oxidation catalyst comprising a cobalt containing component at elevated pressures and temperatures in an oxidation solvent system comprising a $C_2$ to $C_6$ monocarboxylic acid, water, or a mixture thereof, to form an oxidation product containing terephthalic acid substantially free of ethylene glycol; and (4) crystallizing and separating from the solvent system resulting crude terephthalic acid having a copper content of less than 10 ppm, but containing organic impurities comprising aromatic aldehydes and/or monocarboxylic aromatic acids having one or more substituent methyl group, while maintaining a temperature in a range of from about 50 ° C. to about 150 ° C.

Processes for recovering terephthalic acid from polyethylene terephthalate resin, advantageously, further comprise: forming terephthalic acid in a liquid phase oxidation of para-xylene. Both the burning of impurities mid the oxidation of para-xylene are, preferably, carried out at temperatures in a range of from about 120° C. to about 240° C. in the presence of an oxidation catalyst comprising cobalt, manganese, and bromine components in a solvent system comprising acetic acid containing from 1 weight percent to 20 weight percent of water in the liquid phase.

Likewise, both the burning of impurities and the liquid phase oxidation of para-xylene are, preferably, carried out together in one or more reaction zones.

Processes for recovering terephthalic acid from polyethylene terephthalate resin, with or without liquid phase oxidation of para-xylene, advantageously, further comprise: (5) reducing at least a portion of the organic impurities in the crude terephthalic acid in an aqueous solution at elevated temperatures and pressures and in the presence of hydrogen and an insoluble catalyst containing a palladium component on a carbon support; (6) separating the insoluble catalyst from the aqueous solution; and (7) crystallizing and separating purified terephthalic acid from the aqueous solution while maintaining the temperature in a range of from about 50 ° C. to about 150 ° C. The resulting purified terephthalic acid has a L*value in a range of from about 95 to about 100, an a*-value in a range of from about $-1$ to about $+1$, and a b*-value in a range of from about 0.5 to about 2.

In another embodiment of this invention, 2,6-naphthalene dicarboxylic acid is recovered from poly(ethylene-2,6-naphthalene) resin in process comprising: (A) depolymerizing poly(ethylene-2,6-naphthalene) resin containing repeating units of 2,6-naphthalene dicarboxylic acid residue and repeating units of ethylene glycol residue linked by ester bonds, in a solvent comprising of a $C_1$ to $C_6$ alcohol, water, or a mixture thereof, under conditions suitable for hydrolysis of ester bonds at temperatures in a range of from about 120° C. to about 320° C. and pressures sufficient to maintain a liquid phase, to form a depolymerization solution consisting of 2,6-naphthalene dicarboxylic acid, ethylene glycol, and impurities comprising components derived from the resin; (B) burning at least a portion of the impurities in a liquid-phase oxidation with an oxygen-containing gas in the presence of an oxidation catalyst comprising a cobalt containing component at elevated pressures and temperatures in an oxidation solvent system comprising a $C_2$ to $C_6$ monocarboxylic acid, water, or a mixture thereof, to form an oxidation product containing 2,6-naphthalene dicarboxylic acid; and (C) separating from the solvent system resulting solid product of crude 2,6-naphthalene dicarboxylic acid containing organic impurities comprising aromatic aldehydes and/or monocarboxylic aromatic acids having one or more substituent methyl group, while maintaining a temperature in a range of from about 25 ° C. to about 150 ° C.

In a preferred embodiment of this invention for obtaining 2,6-naphthalene dicarboxylic acid, the process further comprises: forming 2,6-naphthalene dicarboxylic acid in a liquid phase oxidation of 2,6-dimethyl naphthalene. Both the burning of impurities and the oxidation of 2,6-dimethyl naphthalene are carried out at temperatures in a range of from about 100° C. to about 240° C. in the presence of an oxidation catalyst comprising cobalt, manganese, and bromine components in a solvent system comprising acetic acid containing from 1 weight percent to 20 weight percent of water in the liquid phase.

Advantageously, processes for obtaining 2,6-naphthalene dicarboxylic acid, with or without a liquid phase oxidation of 2,6-dimethyl naphthalene, further comprise: crystallizing and separating from the depolymerization solution a recovered 2,6-naphthalene dicarboxylic acid substantially free of ethylene glycol, but containing impurities, prior to burning at least a portion of the impurities in a liquid-phase oxidation.

A preferred processes for obtaining purified 2,6-naphthalene dicarboxylic acid further comprises: (D) reducing at least a portion of the organic impurities in the crude 2,6-naphthalene dicarboxylic acid in an aqueous solution at elevated temperatures and pressures and in the presence of hydrogen and at least one insoluble Group VIII noble metal-containing catalyst; (E) separating the solid noble metal-containing catalyst from the aqueous solution; and (F) crystallizing and separating from the aqueous solution purified 2,6-naphthalene dicarboxylic acid having an optical density in a range from about 0 to about 5, an ash content of less 20,000 ppm, and/or a metals content of less than 20,000 ppm, while maintaining the temperature in a range of from about 25° C. to about 150° C.

BRIEF DESCRIPTION OF THE INVENTION

Suitable sources of polyester resin for use in this invention include polyester fibers, polyester films, and manufactured articles such as bottles and like containers. Resins are, generally, made up of structural units which are repeated many times to obtain high molecular weight and other desired properties. In polyester resins repeating structural units are made up of dibasic acid residue and, typically, dihydric alcohol residue linked by ester bonds, i.e., units in which acidic hydrogen atoms of a dicarboxylic acid molecule are replaced by a hydrocarbon group. In preferred polyester resin for use in this invention, the repeating structural units are, generally, made up of aromatic acid residue, preferably, from aromatic acids. Carboxyl groups in preferred aromatic acids are either attached directly to an independent benzene ring or to benzene rings of a condensed ring system such as naphthalene, m which two benzene rings have two carbon atoms in common or anthracene in which three rings are similarly connected so that the rings are not independent.

Suitable polyester resins for use in methods producing aromatic acid according to this invention have repeating structural units containing residues of any dicarboxylic acid which can be formed from a corresponding methyl substituted aromatic compound by liquid-phase oxidation with an oxygen-containing gas in the presence of an oxidation catalyst at elevated pressures and temperatures. Polyester resins, for example, which have repeating structural units containing residues of terephthalic acid, naphthalene dicarboxylic acid, 4,4'-oxybis(benzoic acid), 5-tert-butyl-1,3-benzene dicarboxylic acid and the like. Particularly useful are polyester resins which have repeating structural units containing residues of terephthalic acid or 2,6-naphthalene dicarboxylic acid.

An essential element of processes of this invention is that a portion of undesired impurities present with aromatic acid obtained by depolymerization of a polyester (impurities consisting of alcohol and/or other components of the resin) are burned in a liquid-phase oxidation with an oxygen-containing gas in the presence of an oxidation catalyst at elevated pressures and temperatures in an oxidation solvent system consisting of a $C_2$ to $C_6$ monocarboxylic acid, water, or a mixture thereof, to form an oxidation product containing the desired aromatic acid having an improved purity.

Processes according to this invention are particularly useful in recovery of aromatic acid from polyester waste containing metalloorganic components used to color polyester articles, because of the excellent color obtained in polyesters made from the recovered aromatic acid. Copper containing components of polyester waste, for example, copper phthalocyanine ($C_{32}H_{16}CuN_8$) and compounds derived therefrom, cause impurities which are difficult to remove from aromatic acid. Copper levels in aromatic acid produced by processes of this invention are less than 5 ppm, and preferably less than 1 ppm.

In preparation of comminuted polyester resin, polyethylene terephthalate waste is, for example, subjected to the action of a granulator, or a crusher, or a grinding machine to reduce the waste material to a suitable particle size which can be as large as about one-half inch, or about 2 cm, in maximum length and about one-eighth inch, or about 0.5 cm, in thickness.

A useful method for depolymerization of polyesters according to the present invention is the subject of aforementioned U.S Pat. No. 5,095,145, to Rosen, the disclosure of which is incorporated herein by reference. Comminuted polyester scrap is slurried in water and/or polar solvent and heated to a temperature within the range of from about 221° C. to about 316° C. for a period to hydrolyze ester bonds to obtain a solution and/or slurry of crude aromatic acid, such as, terephthalic acid or 2,6-naphthalene dicarboxylic acid.

Suitable solvents for use in a depolymerization step of the method for producing aromatic acid, such as terephthalic acid, naphthalene dicarboxylic acid, and the like, according to this invention include solvent systems which comprise water and/or a polar organic liquid, such as a $C_1$ to $C_6$ alcohol. Preferred alcohols include methanol, ethanol, propanols, butanols, pentanols, and the like. Suitable solvents include, a mixture of alcohol and water, which preferably contains from 1 to 99 weight percent of water, as introduced into the depolymerization reactor.

In one method for recovery of terephthalic acid from polyethylene terephthalate, for example, a depolymerization solution is cooled to precipitate crude acid. The precipitate is, advantageously, separated from aqueous mother liquor which retains most of the recovered ethylene glycol and some impurities. Washing of the precipitate with water or other polar solvent further removes solubles present with the crude acid.

Suitable solvents for use in an oxidation step of the method for producing purified aromatic acid, such as terephthalic acid, naphthalene dicarboxylic acid, mid the like, for use in combination with the method of this invention include any aliphatic $C_2$ to $C_6$ monocarboxylic acid such as acetic acid, propionic acid, n-butyric acid, isobutyric acid, n-valeric acid, trimethylacetic acid, and caproic acid and water and mixtures thereof. Preferably, the solvent is a mixture of acetic acid, and water, which more preferably contains from 1 to 20 weight percent of water, as introduced into the oxidation reactor. Since heat generated by the highly exothermic oxidation in the liquid-phase is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude aromatic acid product from the product stream, at least a portion of the mother liquor (solvent) in the resulting product stream is generally recycled to the reactor.

A source of molecular oxygen (diatomic oxygen) employed in the oxidation step of a method for producing purified aromatic acid for use in combination with the method of this invention can vary in molecular oxygen content from that of air to oxygen gas. Air is a preferred source of molecular oxygen. In order to avoid formation of explosive mixtures, oxygen-containing gas fed to the oxidation reactor should provide an exhaust gas-vapor mixture containing from about 0.5 to about 8 volume percent oxygen, measured on a solvent-free basis. For example, a feed rate of oxygen-containing gas sufficient to provide oxygen in an amount of from about 1.5 to about 2.8 moles per methyl group will provide about such 0.5 to 8 volume percent oxygen, measured on a solvent-free basis in the vapor condenser.

Catalyst employed in the oxidation step of a method for producing purified aromatic acid for use in combination with the method of this invention comprises cobalt, manganese, and bromine components, and can additionally comprise accelerators known in the art. The weight ratio of cobalt, calculated as elemental cobalt, in the cobalt component of the catalyst-to-polyalkyl aromatic compounds in the liquid-phase oxidation is in the range of from about 0.2 to about 10 milligram atoms (mga) per gram mole of polyalkyl aromatic. The weight ratio of manganese, calculated as elemental manganese, in the manganese component of the catalyst-to-cobalt, calculated as elemental cobalt, in the cobalt component of the catalyst in the liquid-phase oxidation is in a range of from about 0.2 to about 10 mga per mga of cobalt. The weight ratio of bromine, calculated as elemental bromine, in the bromine component of the catalyst-to-total cobalt and manganese, calculated as elemental cobalt and elemental manganese, in the cobalt and manganese components of the catalyst in the liquid-phase oxidation is in a range of from about 0.2 to about 1.5 mga per mga of total cobalt and manganese.

Each of the cobalt and manganese components can be provided in any of its known ionic or combined forms that provide soluble forms of cobalt, mangamese, and bromine in the solvent in the reactor. For example, when the solvent is an acetic acid medium, cobalt and/or manganese carbonate, acetate tetrahydrate, and/or bromine can be employed. The 0.2:1.0 to 1.5:1.0 bromine-to-cobalt and manganese milligram atom ratio is provided by a suitable source of bromine. Such bromine sources include elemental bromine ($Br_2$), or ionic bromide, e.g., HBr, NaBr, KBr, $NH_4Br$, etc., or organic bromides which are known to provide bromide ions at operating temperature of oxidation, e.g., bromobenzenes, benzylbromide, mono- and di-bromoacetic acid, bromoacetyl bromide, tetra-bromoethane, ethylene-dibromide, etc. Total bromine in molecular bromine and ionic bromide is used to determine satisfaction of the elemental bromine-to-total cobalt and manganese milligram atom ratio of 0.2:1.0 to 1.5:1.0. Bromine ion released from the organic bromides at operating conditions of oxidation can be readily determined by known analytical means. Tetra-bromoethane, for example, at operating temperatures of 170° C. to 225° C. has been found to yield about 3 effective gram atoms of bromine per gram mole.

In operation, minimum pressure at which the oxidation reactor is maintained is that pressure which will maintain a substantial liquid phase of the polyalkyl aromatic compounds and at least 70 percent of the solvent. Polyalkyl aromatic compounds and solvent not in the liquid phase because of vaporization are removed from the oxidation reactor as a vapor-gas mixture, condensed, and then returned to the oxidation reactor. When the solvent is an acetic acid-water mixture, suitable reaction gauge pressures in the oxidation reactor are in a range of from about 0 $kg/cm^2$ to about 35 $kg/cm^2$, and typically are in a range of from about 0 $kg/cm^2$ to about 35 $kg/cm^2$. Temperatures within the oxidation reactor range, generally, from about 120° C., preferably from about 150° C., to about 240° C., preferably to about 230° C. Residence time of solvent in the oxidation reactor is generally from about 20 to about 150 minutes and preferably from about 30 to about 120 minutes.

Crude terephthalic acid produced by a liquid-phase oxidation of para-xylene is generally purified by reduction of impurities therein, for example, by methods disclosed in the aforementioned U.S. Pat. Nos. 3,584,039; 3,726,915; and 4,405,809. The purification step of the method for producing purified terephthalic acid for use in combination with methods of the present invention is conducted at an elevated temperature and pressure in a fixed catalyst bed. Crude terephthalic acid to be purified is dissolved in water or a like polar solvent. Although water is a preferred solvent, other suitable polar solvents include relatively lower molecular weight alkyl carboxylic acids, alone or admixed with water. Suitable reactor temperatures for use in this purification step are in a range of from about 100° C. to about 350° C. Preferably, temperatures employed in the purification step are in a range of from about 275° C. to about 300° C.

The purification step of the instant invention can be carried out in a batch mode as well as a continuous mode. For commercial scale purification of terephthalic acid a continuous mode is preferred. In any event, however, a*-value and b*-value of crude terephthalic acid and purified terephthalic acid are monitored so as to obtain a desired color lever of final product, a fiber-grade terephthalic acid.

Terephthalic acid concentration in the solution to be purified by hydrogenation can vary over a relatively wide range. Concentration can be as low as about 5 percent by weight or as high as about 35 percent by weight, based on the weight of the solution. Preferably, the solution concentration of terephthalic acid is in a range of from about 10 to about 30 percent by weight.

Pressure employed in the purification step depends primarily upon the temperature employed therein. Inasmuch as the temperatures at which practical amounts of the impure terephthalic acid may be dissolved in an aforesaid solvent are substantially above the normal boiling point of the solvent, the process pressures are necessarily considerably above atmospheric pressure to maintain the aqueous solution in a liquid phase. If the reactor is hydraulically full, the reactor pressure can be controlled by the feed pumping rate. If the reactor has a head space, the reactor pressure can be maintained by gaseous hydrogen alone or in admixture with an inert gas such as water vapor and or nitrogen in the head space. Use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in a range of about 200 to about 1,500 pounds per square inch gauge (psig), and usually is in a range of about 900 psig to about 1,200 psig.

The reactor employed in the purification step can be operated in several modes. For example, a predetermined liquid level can be maintained in the reactor, and hydrogen can be fed in, for any given reactor pressure, at a rated sufficient to maintain the predetermined liquid level. The difference between the actual reactor pressure and the vapor pressure of the terephthalic acid solution present is the hydrogen partial pressure in the reactor vapor space. Alternatively, if hydrogen is fed in admixture with an inert gas such as nitrogen, the difference between the actual reactor pressure and the vapor pressure of the terephthalic acid solution present is the combined partial pressure of hydrogen and the inert gas admixed therewith. In this case the hydrogen partial pressure can be calculated from the known relative mounts of hydrogen and inert gas present in the admixture.

In yet another operating mode, the reactor can be filled with the terephthalic acid solution so as to provide no reactor vapor space, that is, the reactor can be operated as a hydraulically full system with dissolved hydrogen being fed to the reactor under flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in a range of from about 10 psi to about 200 psi, or higher, depending upon the service pressure rating of the reactor, the degree of contamination of the impure terephthalic acid, the activity and age of the particular catalyst employed, and like processing considerations.

In the operating mode where process control is effected by adjusting directly the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution.

In general, the mount of hydrogen supplied to the purification reactor under reaction conditions is, of course, sufficient to effect the desired hydrogenation.

As described in the aforementioned U.S. Pat. Nos. 3,584,039; 3,726,915; and 4,405,809, catalysts that are suitable for use in the aforesaid purification step are insoluble under the conditions employed therein and comprise at least one supported or unsupported Group VIII noble metal, whose class includes palladium, rhodium, ruthenium, osmium, iridium, and platinum. Preferably, the noble metal is at least one member of the group consisting of palladium and rhodium. Other catalysts effective for aqueous liquid-phase hydrogenation under the relatively mild hydrogenation conditions described herein above are listed in Kirk-Othmer, *Encyclopedia of Chemical Technology*, Wiley-Interscience, particularly in chapters on Hydrogenation and Catalysts. See also U.S. Pat. No. 2,070,770 to Amend and U.S. Pat. No. 2,105,664 to Lazier.

A preferred method for hydrogenation of crude 2,6-naphthalene dicarboxylic acid according to the present invention is the subject of U.S. Pat. No. 5,256,817 to Sikkenga and Hoover, the disclosure of which is incorporated herein by reference.

Preferably, the catalyst comprises a support. Preferred support materials include carbon and charcoal. Typically, the catalyst carrier is active carbon, usually that derived from coconut charcoal in the form of granules having a surface area of at least about 600 $m^2/g$ measured by the BET method using nitrogen. Other porous carbonaceous supports or substrates can, however, be used as long as the surface area requirements can be met. In addition to coconut charcoal, activated carbon derived from other plant or from animal sources can be utilized.

The noble metal component is present on the carrier at a concentration level in a range of from about 0.01 weight percent to about 2 weight percent, based on total weight of catalyst, i.e., metal plus active carbon carrier, mad calculated as the elemental noble metal. Preferably, the catalyst metal loading is about 0.5 weight percent.

A typical catalyst of palladium on a support comprises from about 0.01 weight percent to about 2 weight percent of palladium, based on total weight of catalyst and calculated as elemental metal. The support or carrier for the palladium is porous and inert, and preferably is active carbon having a surface area of about 600 $m^2/g$ to about 1,500 $m^2/g$. Suitable supports for Pd/C hydrogenation catalysts are well-known and are described, inter alai, in U.S. Pat. No. 3,584,039 to Meyer.

A suitable palladium-on-carbon catalyst can be obtained, for example, from Engelhard Corporation, Newark, N.J., under the designation "Palladium on Activated Carbon Granules (Carbon Code CG-5)." Similarly, suitable rhodium-on-carbon catalysts can be obtained from Engelhard Corporation, under the designations "Rhodium on Activated Carbon Granules (carbon Code CG-5)" and "Rhodium on Activated Carbon Granules (carbon Code CG-21 )." Both of these catalysts have a BET; $N_2$ surface area of about 1,000 $m^2/g$ and have a particle size of 4×8 mesh, U.S. Sieve Series. Other suitable rhodium-on-carbon catalysts of similar size and surface area are available from Johnson Matthey Inc., Seabrook, N.H., under the designation "11766 Rhodium, 1% on Steam Activated Carbon Granules, Anhydrous."

Space velocity reported as weight of crude terephthalic acid solution per weight of catalyst per hour in the purification step is in a range of from about 5 $hours^{-1}$ to about 25 $hours^{-1}$, preferably from about 10 $hours^{-1}$ to about 15 $hours^{-1}$. Residence time of the solution in the catalyst bed varies, depending upon activity of catalysts present.

The color level of crude terephthalic acid, purified terephthalic acid product, and polyethylene terephthalate can be monitored or evaluated directly or indirectly, as described herein below. Partial pressure of hydrogen in the reactor can be adjusted to compensate for any detected impermissible deviation of the purified terephthalic acid from the desired color level. Adjustment can be made by the procedure taught in U.S. Pat. No. 4,782,181, which is incorporated herein by reference.

In one aspect, color level of crude terephthalic acid, purified terephthalic acid product, and polyethylene terephthalate can be ascertained by measuring its $b^*$-value on the Hunter Color Scale as described in Hunter, The Measurement of Appearance, Chapter 8, pp. 103 to 132, John Wiley & Sons, N.Y. (1975), and in Wyszecki et al., Color Science Concepts and Methods, Quantitative Data and Formulae, 2d Ed., pp. 166 to 168, John Wiley & Sons, N.Y. (1982).

More specifically, b*-values of crude terephthalic acid, purified terephthalic acid product, and polyethylene terephthalate can be determined using, for example, a Diano Match Scan Spectrophotometer as follows. A sample of solid product is pressed into a pellet having a thickness of about 0.25 inch and a diameter of about 1 inch. The pellet is then irradiated with white light that has been UV-filtered. The spectrum of visible light reflected from the sample is determined and tristimulus values (X, Y, and Z) are computed using the CIE Standard Observer functions. Using a weighted-ordinate method, tristimulus values are obtained from the following equations:

$$X = \sum_{400}^{700} R\lambda\, x\lambda,\ Y = \sum_{400}^{700} R\lambda\, y\lambda,\ Z = \sum_{400}^{700} R\lambda\, z\lambda,$$

where $R\lambda$ is the percent reflectance of the pellet at wavelength X and $x\lambda$, $y\lambda$, and $z\lambda$ are Standard Observer functions at wavelength 1 for CIE Illuminated D65. Tristimulus values X, Y, and Z, identify the color of the pellet in terms of a mixture of primary colors that match it visually. Tristimulus values, however, are of limited use as color specifications, because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CIE 1976 L*a*b* formula which converts tristimulus values to L*, a*, and b* values as shown below:

$L^* = 25\,(100\, Y/Y_0)^{\frac{1}{3}} - 16$ $a^* = 500\,[(X/X_0)^{\frac{1}{3}} - (Y/Y_0)^{\frac{1}{3}}]$ $b^* = 500\,[(Y/Y_0)^{\frac{1}{3}} - (Z/Z_0)^{\frac{1}{3}}]$ The L* value is a measure of the luminosity or whiteness of an object where a L* value of 100 is pure white, a L* value of 0 is black, and values in a range $0 < L^* < 100$ are gray. The L* value is strictly a function of tristimulus Y-value. The b*-value is a measure of a yellowness-blueness attribute where positive b*-values represent yellow appearance and negative b*-values represent blue appearance. The b*-value is a function of both tristimulus values Y and Z.

Alternatively, by the aforesaid indirect method, the color level, e.g., b*-value, of purified terephthalic acid product can be correlated with optical density of (OD) of incoming feed and utilized to adjust the partial pressure of hydrogen in the reactor. Typically, optical density values can be determined using a spectrophotometer and a light beam having wavelength of 340 nanometers (nm) or millimicrons (mu), correlated with b*-value of purified terephthalic acid product at specific partial pressure of hydrogen for a given catalyst and then used to adjust the partial pressure of hydrogen during a particular process run so as to produce purified product having the desired b*-value.

It has been found that a 0.1 unit deviation in b*-value of purified terephthalic acid product can be compensated by an adjustment in partial pressure of hydrogen in the reactor of as low as about 5 psi to as high as about 60 psi depending upon activity of catalyst employed. If a fresh, relatively high activity catalyst is used, an initial adjustment in partial pressure of hydrogen required for a 0.1 unit deviation in b*-value is, usually, in a range of from about 5 psi to about 7.5 psi. As catalyst stabilizes, however, the adjustment in partial pressure of hydrogen required for a 0.1 unit deviation in b*-value is, usually, in a range of from about 40 psi to about 50 psi.

It has been found that a 0.1 unit change in optical density at 340 nm ($OD_{340}$) of feed solution correlates with about 0.05 unit change in b*-value of purified terephthalic acid product which is obtained from that particular feed solution. Thus, a 0.1 unit change in $OD_{340}$-value of the feed solution can, usually, be compensated by an adjustment in partial pressure of hydrogen in the reactor in a range of from about 2.5 psi to about 4 psi for a fresh, relatively high activity catalyst. As activity of a catalyst stabilizes during use, however, a 0.1 unit change in $OD_{340}$-value of the feed solution can, usually, be compensated by an adjustment in partial pressure of hydrogen in the reactor in a range of from about 20 psi to about 25 psi.

An overall relationship among b*-value, partial pressure of hydrogen in the reactor, and $OD_{340}$ can also be expressed as $$b^*\text{-value } \alpha\ A\,(H_{2pp}) + C\,(Ob_{340})$$

where $H_{2pp}$ designates partial pressure of hydrogen in the reactor expressed in psi, $OD_{340}$ is the optical density value of crude terephthalic acid feed solution of the reactor, A is a number in a range of from about 0.001 to about 0.03, and C is a number in a range of from about 0.4 to about 1.4.

Similarly, an overall relationship among b*-value, concentration of hydrogen in the reactor solution, and optical density at 340 nm can be expressed as $$b^*\text{-value } \alpha\ D\,(H_{2conc.}) + C\,(OD_{340})$$

where $H_{2conc.}$ designates concentration of hydrogen in the reactor expressed in cubic centimeters of hydrogen at 1 atmosphere absolute pressure and 0° C. dissolved per gram of crude terephthalic acid feed solution, $OD_{340}$ is the optical density value of crude terephthalic acid feed solution of the reactor, D is a number in a range of from about 0.2 to about 5.75, and C is a number in a range of from about 0.4 to about 1.4.

If it is desired to modulate the concentration of hydrogen in the solution in a hydraulically full reactor directly by adjusting flow of gaseous hydrogen to the hydrogenation reactor, then in such an event hydrogen flow rate can be adjusted to provide a change in concentration of hydrogen in a range of from about 0.03 cc/g to about 0.3 c/g for a 0.1 unit change in b*-value of the product to be implemented, or in a range of about 0.015 cc/g to about 0.15 cc/g for an observed 0.1 unit change in $OD_{340}$ of feed solution to the hydrogenation reactor.

EXAMPLES OF THE INVENTION

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLE 1

In Examples 1 and 2 crude terephthalic acid was recovered from post-consumer polyethylene terephthalate flake containing copper phthalocyanine ($C_{32}H_{16}CuN_8$) and/or compounds derived therefrom, by simultaneous reaction of polyethylene terephthalate and para-xylene under conditions of liquid-phase oxidation of para-xylene in a solvent; the resulting crude terephthalic acid, which contained no detectable copper, was purified by hydrogenation in an aqueous solution. In Example 1 the resulting purified terephthalic acid was polyesterified to form polyethylene terephthalate resins having excellent color.

Depolymerization and Oxidation

A 2 L titanium reactor was charged with acetic acid (875 g), distilled-deionized water (120.4 g), hydrobromic acid (1.61 g of 48 aqueous HBr), cobalt (II) acetate (1.23 g, $Co(C_2H_3O_2)_2.4H_2O$), manganese (II) acetate (3.29 g, $Mn(C_2H_3O_2)_2.4H_2O$), and a commercially available waste green polyethylene terephthalate flake (180 g) containing about 8 ppm copper. Typically, measurement of color level for waste polyethylene terephthalate resin from green beverage bottles gave an a*-value of about −27 (green), and a b*-value of about 13 (yellow). The reactor was heated to 220° C. under nitrogen. para-Xylene was fed to the reactor at a rate of 3.3 g/min and air was fed to the reactor at 0.76 SCFM. As oxidation proceeded, temperature of the liquid phase increased to about 230° C. After 60 min the air and para-xylene feeds were shut off and the reactor contents cooled to a temperature of about 90° C. Resulting crude product (360 g) was recovered by filtration, washed with about 300 g of fresh acetic acid, and dried. This crude crude terephthalic acid product was identified as Crude TA-1. Analysis of Crude TA-1 found that it contained less than 0.9 ppm of copper, 940 ppm of 4-carboxybenzaldehyde, and 327 ppm of para-toluic acid. Measurement of color level for Crude TA-1 gave a L*-value of 93.7, an a*-value of -0.68, and a b*-value of 4.96.

Hydrogenation

A 1 gal stainless steel autoclave was charged with the crude terephthalic acid (Crude TA-1, 20 percent acid in water) and a palladium on carbon hydrogenation catalyst (0.5 % Pd/C). This mixture was treated with hydrogen at 280° C. for two hours. After cooling the resulting solution to ambient temperature, purified terephthalic acid product was recovered by filtration. The filter cake was washed with water and dried. Analysis of this crude product found that it contained less than the detectable limit of copper (<0.9 ppm), 23 ppm of 4-carboxybenzaldehyde, and 8 ppm of para-toluic acid. Measurement of color level for this crude terephthalic acid gave a L*-value of 96.7, an a*-value of -0.31, and a b*-value of 1.12.

Esterification

A 2 L stainless steel autoclave was charged with a composite of purified terephthalic acid prepared by the above procedure from post-consumer polyethylene terephthalate flake (835 g) and purified terephthalic acid prepared by oxidation of para-xylene (65 g), ethylene glycol (405 g), choline (0.064 g), $SbO_3$ (0.25 g), and $H_3PO_4$ (0.1009 g). The autoclave and this esterification mixture was heated to 285° C. Measurement of color level for this polyethylene terephthalate product gave a L*-value of 83.0, an a*value of −0.66, and a b*-value of 3.47.

EXAMPLE 2

In this example a slurry was prepared from granulated polyethylene terephthalate and heated to a temperature of 120° C. without substantial depolymerization. Preheated slurry was fed into a continuous liquid-phase oxidation of para-xylene where simultaneous reaction of the polyethylene terephthalate and oxidation of para-xylene formed terephthalic acid.

Slurry Preparation

A 5 gal titanium vessel complete with stirring means, external heating jacket, and thermocouple, was charged with a slurry (20% solids) of waste polyethylene terephthalate powder (L*-value of 82, an a*-value of −26 (green), and a b*-value of 13 (yellow), and a copper level of 4 ppm), in aqueous acetic acid (70% acetic acid). The charged slurry vessel heated to a temperature of about 115 ° C. The reactor was maintained at temperatures in a range of from about 115° C. to about 120° C.

Continuous Oxidation

A continuous liquid-phase oxidation of para-xylene was initiated in a 3 gal titanium reactor. Feed rates into the oxidation reactor were: 0.60 lb/hr of para-xylene; 2.48 lb/hr of acetic acid; 0.169 lb/hr of water; 0.0033 lb/hr of hydrobromic acid (48 % aqueous HBr), 0.0023 lb/hr of cobalt (II) acetate ($Co(C_2H_3O_2)_2.4H_2O$), 0.0041 lb/hr of manganese (II) acetate ($Mn(C_2H_3O_2)_2.4H_2O$) and 41 SCFH of air. As oxidation proceeded, small portions of depolymerization products were "slugged" into the continuous liquid-phase oxidation of para-xylene at a rated of S to 7 slugs/hr to provide a rate of 3.41 lb/hr. Once feeding preheated slurry into the continuous oxidation began, the air flow rate was increased to 47 SCFH to maintain a 3 % oxygen level in the vent gas from the oxidation reactor. Oxidation was carried out at a temperature of about 215° C. and a pressure of about 340 psig. Residence time was 112 minutes and oxidation reactor effluent flow rate was 4.53 lb/hr. Crude terephthalic acid product was recovered by filtration from the resulting slurry, washed, and dried. This crude terephthalic acid product was identified as Crude TA-2. Analysis of Crude TA-2 found that it contained less than 0.5 ppm of copper, and 500 ppm of 4-carboxybenzaldehyde. Measurement of color level for Crude TA-2 gave a L*-value of 96.7, an a*-value of −0.32, and a b*-value of 2.37.

EXAMPLE 3

This example demonstrates, depolymerization of waste polyethylene terephthalate from green beverage bottles containing copper phthalocyanine ($C_{32}H_{16}CuN_8$) and/or compounds derived therefrom, and separation of solid terephthalic acid by filtration from the resulting mother liquor. Impurities separated with the terephthalic acid are, thereafter, burned in a liquid-phase oxidation of para-xylene and copper removed from the terephthalic acid.

Depolymerization

A 1 gal titanium reactor complete with stirring means, external heating jacket, and thermocouple, was charged with 199.3 g of waste polyethylene terephthalate resin from green beverage bottles, cut into about ¼ inch by ¼ inch squares, and 1204.5 g of distilled-deionized water. Typically, measurement of color level for waste polyethylene terephthalate resin from green beverage bottles gave an a*-value of about −27 (green), and a b*-value of about 13 (yellow). The charged reactor was purged with nitrogen four times to a pressure of 400 psig, closed, and heated to a temperature of about 275° C. over a period of 100 minutes. The reactor was maintained at a temperature of about 275° C. for one additional hour. The reactor was allowed to cool to 25° C. and solid terephthalic acid filtered from the resulting mixture. The mother liquor was found to contain 90% of the amount of ethylene glycol calculated on the basis of the resin charged to the reactor. After drying, the solid terephthalic acid powder weighted 151.0 g (a yield of 87.6% of the amount of terephthalic acid calculated on the basis of the resin charged to the reactor). Analysis of the powder found a copper content of 5.2 ppm. Measurement of color level for this terephthalic acid powder gave a L*-value of 90, an a*-value of −1.7, and a b*-value of 4.5.

Oxidation

A 2 L titanium reactor was charged with acetic acid (875 g), distilled-deionized water (120.4 g), hydrobromic acid (1.61 g of 48 aqueous HBr), cobalt (II) acetate (1.23 g, $Co(C_2H_3O_2)_2.4H_2O$), manganese (II) acetate (3.29 g, $Mn(C_2H_3O_2)_2.4H_2O$), and terephthalic acid powder recovered as described above from beverage bottles (156 g, containing 5.2 ppm of copper). The reactor was heated to 430° F. under nitrogen. Then para-xylene was fed to the reactor at a rate of 3.32 g/min and air was fed to the reactor at 0.42 SCFM. As oxidation proceeded, temperature of the liquid phase increased to about 230° C. After 60 min the air and para-xylene feeds were shut off and the reactor contents cooled to ambient temperature. Crude terephthalic acid product was recovered by filtration from the resulting slurry, washed with about 370 g of fresh acetic acid, and dried (370 g, a yield of 79% of the mount of terephthalic acid calculated on the basis of the resin charged to the reactor). Analysis of this crude product found that it had a copper content of 0.5 ppm. Measurement of color level for this terephthalic acid gave a L*-value of 93.7, an a*-value of −0.68, and a b*-value of 4.96.

EXAMPLE 4

This example demonstrates, depolymerization of waste polyethylene terephthalate resins from green beverage bottles containing copper phthalocyanine ($C_{32}H_{16}CuN_8$) and/or compounds derived therefrom, in a first reactor to form a depolymerization mixture containing terephthalic acid, ethylene glycol, and other impurities derived from the resins. The depolymerization mixture was "slugged" into a continuous liquid-phase oxidation of para-xylene where ethylene glycol and other impurities were burned. Recovered crude terephthalic acid contained no detectable copper.

Depolymerization

A 5 gal titanium reactor complete with stirring means, external heating jacket, and thermocouple, was charged with a slurry (20% solids) of waste polyethylene terephthalate powder (L*-value of 82, an a*-value of −26 (green), and a b*-value of 13 (yellow), and a copper level of 3 ppm), in aqueous acetic acid (70% acetic acid). The charged reactor was purged with nitrogen, closed, and heated to a temperature of about 215° C. over a period of 3.5 hours. The reactor was maintained at temperatures in a range of from about 215° C. to about 220° C. for 40 additional minutes. The resulting mixture of depolymerization products in the reactor was sampled. Analysis of recovered cake and mother liquor showed the that 98% of the copper was present in the cake which was 99% terephthalic acid and mother liquor was 6% ethylene glycol. Measurement of color level for the cake gave a L*-value of 90, an a*-value of −4.5, and a b*-value of −2.1.

Oxidation

A continuous liquid-phase oxidation of para-xylene was initiated in a 3 gal titanium reactor. Feed rates into the oxidation reactor were: 0.92 lb/hr of para-xylene; 3.7 lb/hr of acetic acid; 0.26 lb/hr of water; 0.0051 lb/hr of hydrobromic acid (48% aqueous HBr), 0.0035 lb/hr of cobalt (II) acetate ($Co(C_2H_3O_2)_2.4H_2O$), 0.0062 lb/hr of manganese (II) acetate ($Mn(C_2H_3O_2)_2.4H_2O$) and 64 SCFH of air. As oxidation proceeded, small portions of depolymerization products were "slugged" into the continuous liquid-phase oxidation of para-xylene at a rated of 5 to 7 slugs/hr to provide a rate of 2.1 lb/hr. Once feeding the products of depolymerization into the continuous oxidation began, the air flow rate was increased to 71 SCFH to maintain a 3% oxygen level in the vent gas from the oxidation reactor. Oxidation was carried out at a temperature of about 215°C. and a pressure of about 360 psig. Residence time was 112 minutes and oxidation reactor effluent flow rate was 4.5 lb/hr. Crude terephthalic acid product was recovered by filtration from the resulting slurry, washed, and dried. Analysis of this crude product found that it contained less than 0.9 ppm of copper, 950 ppm of 4-carboxybenzaldehyde, and 270 ppm of toluic acid. Measurement of color level for this terephthalic acid gave a L*-value of 96.7, an a*-value of −1.44, and a b*-value of 2.25.

Comparative Examples A and B

Comparative Examples A and B illustrate the poor color of terephthalic acid by depolymerizing waste green polyethylene terephthalate in an aqueous mixture, with and without acetic acid, at elevated temperatures and pressures which maintain the aqueous mixture in the liquid phase, but without liquid-phase oxidation, i.e., without using oxygen-containing gas and oxidation catalyst.

Comparative Example A

A sample of waste green polyethylene terephthalate from beverage bottles, 250 lbs, in the form of ¼ inch squares was depolymerized. The sample was charged to a 250 gal stainless steel reactor with deionized water. The reactor was complete with stirring means, a thermocouple and external means for heating. After the charged reactor was purged with nitrogen, the reactor was closed and heated over a period of about 3 hours to a temperature in a range of from 240° C. to 245° C. and maintained at such temperatures for a period of about 1 hour. The reactor and resulting mixture were allowed to cool to room temperature to precipitate crude terephthalic acid. A sample of this crude terephthalic acid, identified as Comparative Example A, was then taken and analyzed for color. Comparative Example A had L*-value of 81.31, a*-value of −7.55, and b*-value of −0.63.

Comparative Example B

A sample of waste green polyethylene terephthalate from beverage bottles which had a*-value of -27 and b*-value of 13, was depolymerized. The sample was charged to a one gallon titanium reactor with 70 percent acetic acid in distilled and deionized water. The reactor was complete with stirring means, a thermocouple and external means for heating. After the charged reactor was purged with nitrogen, the reactor was closed and heated over a period of hours to a temperature in a range of from 215° C. to 220° C. and maintained at elevated temperature for a period of hours. The reactor and resulting mixture were allowed to cool. Crude terephthalic acid product was recovered by filtration from the resulting slurry, washed, and dried. A sample of this crude terephthalic acid, identified as Comparative Example B, was then taken and analyzed as 99% terephthalic acid. Comparative Example B had L*-value of 91.43, a*-value of -4, and b*-value of -2.

These results are in contrast to an a*-value of -0.3, and a b*value of +2 for crude terephthalic acid obtained from a sample of the same waste green polyethylene terephthalate which was depolymerized by the depolymerization step of the instant invention.

Comparative Example C

Comparative Example C illustrates the very poor color of polyethylene terephthalate made from terephthalic acid obtained by depolymerizing waste green polyethylene terephthalate and hydrogenation, but without liquid-phase oxidation, i.e., without using oxygen-containing gas and oxidation catalyst.

Depolymerization of green polyethylene terephthalate waste was carried out as in Example 4, except using water without acetic acid as solvent at temperatures of from about 270° C. to about 275° C. After a crude terephthalic acid cake was separated from mother liquor, washed, and dried, the crude terephthaiic acid was hydrogenated and polyesterflied as in Example 1. Polyethylene terephthalate obtained, identified as Comparative Example C, was analyzed for color. Comparative Example C had L*-value of 79.13, a*-value of -5.41, and b*-value of -7.23.

These results are in contrast to a L*-value of 83.0, an a*-value of -0.66, and a b*-value of 3.47 polyethylene terephthalate obtained in Example 1, which used liquid-phase oxidation in accordance with the instant invention.

EXAMPLE 5

In the following example crude 2,6-naphthalene dicarboxylic acid was recovered from poly(ethylene-2,6-naphthalene) resin by simultaneous reaction of poly( ethylene-2,6-naphthalene ) resin and 2,6-dimethyl naphthalene under conditions of liquid-phase oxidation of 2,6-dimethyl naphthalene in a solvent.

Depolymerization and Oxidation

A 1 L titanium reactor was charged with acetic acid (617.3 g), distilled-deionized water (32 g), hydrobromic acid (5.2 g of 48% aqueous HBr), cobalt (II) acetate (3.8 g, $Co(C_2H_3O_2)_2.4H_2O$), manganese (II) acetate (11.4 g, $Mn(C_2H_3O_2)_2.4H_2O$), and a commercially produced poly( ethylene-2,6-naphthalene ) resin ground to 1 mm particle size. The reactor was heated to 180©C. under nitrogen. Then 2,6-dimethyl naphthalene was fed to the reactor at a rate of 2 mL/min and air was fed to the reactor at 0.25 SCFM. As oxidation proceeded, temperature of the liquid phase increased to about 200° C. After 70 min the air and 2,6-dimethyl naphthalene feeds were shut off and the reactor contents cooled to a temperature of about 90° C. Crude product was recovered by filtration, washed with about 200 g of fresh acetic acid, and dried. Recovered crude 2,6-naphthalene dicarboxylic acid product weighed 360 g.

That which is claimed is:

1. A process for recovering dibasic aromatic acid from polyester resin comprising repeating units of dibasic aromatic acid residue and repeating units of dihydric alcohol residue linked by ester bonds which process comprises:
    depolymerizing polyester resin in a solvent under conditions suitable for hydrolysis of ester bonds to form a mixture containing a solution of aromatic acid and impurities consisting of alcohol and other components of the resin;
    burning at least a portion of the impurities in a liquid-phase oxidation with an oxygen-containing gas in the presence of an oxidation catalyst at elevated pressures and temperatures in an oxidation solvent system consisting of a $C_2$ to $C_6$ monocarboxylic acid, water, or a mixture thereof, to form an oxidation product containing aromatic acid; and
    separating from the oxidation solvent system resulting solid product of crude dibasic aromatic acid substantially free of alcohol, but containing organic impurities.

2. The process according to claim 1 wherein both the depolymerizing of polyester resin and the liquid phase oxidation are carried out together in one or more reaction zones.

3. The process according to claim 1 wherein the process further comprises:
    reducing at least a portion of the organic impurities in the crude dibasic aromatic acid in an aqueous solution at elevated temperatures and pressures and in the presence of hydrogen and at least one insoluble Group VIII noble metal-containing catalyst;
    separating the solid noble metal-containing catalyst from the aqueous solution; and
    crystallizing and separating purified dibasic aromatic acid from the aqueous solution.

4. The process according to claim 3 wherein the dibasic aromatic acid is terephthalic acid, the noble metal is at least one member of the group consisting of palladium and rhodium, and the purified dibasic aromatic acid has a total metals content of less than 100 ppm and contains less than 1000 ppm total of 4-carboxybenzaldehyde and toluic acid.

5. A process for recovering terephthalic acid from polyethylene terephthalate resin comprising repeating units of terephthalic acid residue and repeating units of ethylene glycol residue linked by ester bonds which process comprises:
    depolymerizing polyethylene terephthalate resin in a solvent comprising of a $C_1$ to $C_6$ alcohol, water, or a mixture thereof, under conditions suitable for hydrolysis of ester bonds at temperatures in a range of from about 120° C. to about 320° C. and pressures sufficient to maintain a liquid phase, to form a depolymerization solution consisting of terephthalic acid, ethylene glycol, and impurities comprising components derived from the resin;
    burning at least a portion of the impurities in a liquid-phase oxidation with an oxygen-containing gas in the presence of an oxidation catalyst comprising a cobalt containing component at elevated pressures and temperatures in an oxidation solvent system comprising a $C_2$ to $C_6$ monocarboxylic acid, water, or a mixture thereof, to form an oxidation product containing terephthalic acid; and crystallizing and separating from the oxidation solvent system resulting crude terephthalic acid having a total metals content of less than 100 ppm, but containing organic impurities comprising aromatic aldehydes and/or monocarboxylic aromatic acids having one or more substituent methyl group, while maintaining a temperature in a range of from about 50° C. to about 150° C.

6. The process according to claim 5 further comprising:

crystallizing and separating from the depolymerization solution a recovered terephthalic acid substantially free of ethylene glycol, but containing color-causing impurities, prior to burning at least a portion of the color-causing impurities in a liquid-phase oxidation.

7. The process according to claim 5 further comprising:

forming terephthalic acid in a liquid phase oxidation of para-xylene, and wherein both the burning of impurities and the oxidation of para-xylene are carried out at temperatures in a range of from about 120° C. to about 240° C. in the presence of an oxidation catalyst comprising cobalt, manganese, and bromine components in a solvent system comprising acetic acid containing from 1 weight percent to 20 weight percent of water in the liquid phase.

8. The process according to claim 7 wherein both the burning of impurities and the forming terephthalic acid by liquid phase oxidation of para-xylene are carried out together in one or more reaction zones.

9. The process according to claim 7 wherein the depolymerizing of polyethylene terephthalate resin, the burning of impurities and the forming terephthalic acid by liquid phase oxidation of para-xylene are carried out together in one or more reaction zones.

10. The process according to claim 5 wherein the process further comprises:

reducing at least a portion of the organic impurities in the crude terephthalic acid in an aqueous solution at elevated temperatures and pressures and in the presence of hydrogen and at least one insoluble Group VIII noble metal-containing catalyst;

separating the solid noble metal-containing catalyst from the aqueous solution; and crystallizing and separating purified terephthalic acid from the aqueous solution while maintaining the temperature in a range of from about 50° C. to about 150° C.

11. The process according to claim 10 wherein the insoluble Group VIII noble metal-containing catalyst is a palladium containing component on a carbon support, and the purified terephthalic acid has a b*-value less than 10.00 and a metals content of less than 100 ppm.

12. A process for recovering terephthalic acid from waste polyethylene terephthalate resin comprising repeating units of terephthalic acid residue and repeating units of ethylene glycol residue linked by ester bonds which process comprises:

depolymerizing waste polyethylene terephthalate resin in a solvent comprising of a $C_1$ to $C_6$ alcohol, water, or a mixture thereof, under conditions suitable for hydrolysis of ester bonds at temperatures in a range of from about 120° C. to about 320° C. and pressures sufficient to maintain a liquid phase, to form a depolymerization solution consisting of terephthalic acid, ethylene glycol, and impurities comprising copper containing components derived from the resin;

crystallizing and separating from the depolymerization solution a recovered terephthalic acid substantially free of ethylene glycol, but containing impurities comprising copper containing components derived from the resin;

burning at least a portion of the impurities in a liquid-phase oxidation with an oxygen-containing gas in the presence of an oxidation catalyst comprising a cobalt containing component at elevated pressures and temperatures in an oxidation solvent system comprising a $C_2$ to $C_6$ monocarboxylic acid, water, or a mixture thereof, to form an oxidation product containing terephthalic acid substantially free of ethylene glycol; and crystallizing and separating from the solvent system resulting crude terephthalic acid having a copper content of less than 10 ppm, but containing organic impurities comprising aromatic aldehydes and/or monocarboxylic aromatic acids having one or more substituent methyl group, while maintaining a temperature in a range of from about 50° C. to about 150° C.

13. The process according to claim 12 further comprising:

forming terephthalic acid in a liquid phase oxidation of para-xylene, and wherein both the burning of impurities and the oxidation of para-xylene are carried out at temperatures in a range of from about 120° C. to about 240° C. in the presence of an oxidation catalyst comprising cobalt, manganese, and bromine components in a solvent system comprising acetic acid containing from 1 weight percent to 20 weight percent of water in the liquid phase.

14. The process according to claim 12 wherein both the burning of impurities and the liquid phase oxidation of para-xylene are carried out together in one or more reaction zones.

15. The process according to claim 12 wherein the process further comprises:

reducing at least a portion of the organic impurities in the crude terephthalic acid in an aqueous solution at elevated temperatures and pressures and in the presence of hydrogen and an insoluble catalyst containing a palladium component on a carbon support;

separating the insoluble catalyst from the aqueous solution; and crystallizing and separating purified terephthalic acid from the aqueous solution while maintaining the temperature in a range of from about 50° C. to about 150° C., and wherein the resulting purified terephthalic acid has a L*value in a range of from about 95 to about 100, an a*-value in a range of from about −1 to about +1, and a b*-value in a range of from about 0.5 to about 2.

16. A process for recovering 2,6-naphthalene dicarboxylic acid from poly(ethylene-2,6-naphthalene) resin comprising repeating units of 2,6-naphthalene dicarboxylic acid residue and repeating units of ethylene glycol residue linked by ester bonds which process comprises:

depolymerizing poly(ethylene-2,6-naphthalene) resin in a solvent comprising of a $C_1$ to $C_6$ alcohol, water, or a mixture thereof, under conditions suitable for hydrolysis of ester bonds at temperatures in a range of from about 120° C. to about 320° C. and pressures sufficient to maintain a liquid phase, to form a depolymerization mixture consisting of 2,6-naphthalene dicarboxylic acid, ethylene glycol, and impurities comprising components derived from the resin;

burning at least a portion of the impurities in a liquid-phase oxidation with an oxygen-containing gas in the presence of an oxidation catalyst comprising a cobalt containing component at elevated pressures and temperatures in an oxidation solvent system comprising a $C_2$ to $C_6$ monocarboxylic acid, water, or a mixture thereof, to form an oxidation product containing 2,6-naphthalene dicarboxylic acid; and separating from the solvent system resulting solid product of crude 2,6-naphthalene dicarboxylic acid containing organic impurities comprising aromatic aldehydes and/or monocarboxylic aromatic acids having one or more substituent methyl group, while maintaining a temperature in a range of from about 25 ° C. to about 150 ° C.

17. The process according to claim 16 further comprising:

forming 2,6-naphthalene dicarboxylic acid in a liquid phase oxidation of 2,6-dimethyl naphthalene, and wherein both the burning of impurities and the oxidation of 2,6-dimethyl naphthalene are carried out at temperatures in a range of from about 100° C. to about 240° C. in the presence of an oxidation catalyst comprising cobalt, manganese, and bromine components in a solvent system comprising acetic acid containing from 1 weight percent to 20 weight percent of water in the liquid phase.

18. The process according to claim 17 further comprising:

crystallizing and separating from the depolymerization solution a recovered 2,6-naphthalene dicarboxylic acid substantially free of ethylene glycol, but containing impurities, prior to burning at least a portion of the impurities in a liquid-phase oxidation.

19. The process according to claim 17 wherein the process further comprises:

reducing at least a portion of the organic impurities in the crude 2,6-naphthalene dicarboxylic acid in an aqueous solution at elevated temperatures and pressures and in the presence of hydrogen and at least one insoluble Group VIII noble metal-containing catalyst;

separating the solid noble metal-containing catalyst from the aqueous solution; and crystallizing and separating from the aqueous solution purified 2,6-naphthalene dicarboxylic acid having an optical density in a range from about 0 to about 5, an ash content of less 20,000 ppm, while maintaining the temperature in a range of from about 25° C. to about 150 ° C.

20. The process according to claim 16 further comprising:

crystallizing and separating from the depolymerization solution a recovered 2,6-naphthalene dicarboxylic acid substantially free of ethylene glycol, but containing impurities, prior to burning at least a portion of the impurities in a liquid-phase oxidation.

21. The process according to claim 20 wherein the process further comprises:

forming 2,6-naphthalene dicarboxylic acid in a liquid phase oxidation of 2,6-dimethyl naphthalene, and wherein both the burning of impurities and the oxidation of 2,6-dimethyl naphthalene are carried out together in one or more reaction zones at temperatures in a range of from about 120° C. to about 240° C. in the presence of an oxidation catalyst comprising cobalt, manganese, and bromine components in a solvent system comprising acetic acid containing from 1 weight percent to 20 weight percent of water in the liquid phase; and further comprises:

reducing at least a portion of the organic impurities in the crude 2,6-naphthalene dicarboxylic acid in an aqueous solution at elevated temperatures and pressures and in the presence of hydrogen and at least one insoluble Group VIII noble metal-containing catalyst;

separating the solid noble metal-containing catalyst from the aqueous solution; and crystallizing and separating from the aqueous solution purified 2,6-naphthalene dicarboxylic acid having an optical density in a range from about 0 to about 5, a metals content of less than 20,000 ppm, while maintaining the temperature in a range of from about 25° C. to about 150° C.

* * * * *

UNITED STATES PATENT AND TRADEMARK OFFICE
CERTIFICATE OF CORRECTION

PATENT NO. : 5,414,113
DATED : May 9, 1995
INVENTOR(S) : Jeffrey L. Broeker, John A. Macek, Allen B. Mossman, Bruce I. Rosen, Thomas M. Bartos It is certified that error appears in the above-indentified patent and that said Letters Patent is hereby corrected as shown below:

| Col. | Line | |
|---|---|---|
| 16 | 37 | "para-xylene at a rated of S to 7 slugs/hr" should read --para-xylene at a rated 5 to 7 slugs/hr-- |
| 17 | 28 | "(1.23 g, Co(C$_2$H$_3$O$_2$)$_2$·4H$_2$O)," should read --(1.23 g, Co(C$_2$H$_3$O$_2$)$_2$·4H$_2$O),-- |
| 17 | 41-42 | "a yield of 79% of the mount of terephthalic acid" should read --a yield of 79% of the amount of terephthalic acid-- |
| 19 | 66 | "The reactor was heated to 180©C." should read --The reactor was heated to 180°C.-- |

Signed and Sealed this

Thirteenth Day of February, 1996

Attest:

BRUCE LEHMAN

Attesting Officer     Commissioner of Patents and Trademarks